United States Patent [19]
Moodie et al.

[11] Patent Number: 5,862,529
[45] Date of Patent: Jan. 26, 1999

[54] DEVICE FOR PROTECTING FACE AND EYES AGAINST PROJECTILE IMPACT

[75] Inventors: Donald E. Moodie, Marblehead; Paul F. Vinger, Concord, both of Mass.

[73] Assignee: Springuard Technology Group Inc, Concord, Mass.

[21] Appl. No.: 590,296

[22] Filed: Jan. 23, 1996

[51] Int. Cl.$^6$ ........................................ A61F 9/02
[52] U.S. Cl. ........................ 2/431; 2/443; 2/445
[58] Field of Search .................. 2/426, 427, 431, 2/439, 440, 441, 442, 443, 445, 446, 452, 454

[56] References Cited

U.S. PATENT DOCUMENTS

| | | | |
|---|---|---|---|
| 814,127 | 3/1906 | Gamble . | |
| 1,203,564 | 11/1916 | April . | |
| 1,222,002 | 4/1917 | Lajcak . | |
| 2,406,608 | 8/1946 | Joyce | 2/440 |
| 2,914,770 | 12/1959 | Sterne et al. | 2/440 |
| 2,979,729 | 4/1961 | Hirschmann, Jr. | 2/446 |
| 3,694,814 | 10/1972 | De Barbieri et al. | 2/439 |
| 4,173,795 | 11/1979 | Lundin et al. | 2/425 |
| 4,264,988 | 5/1981 | Specht | 2/431 |
| 4,736,466 | 4/1988 | Kallstrom | 2/9 |
| 4,933,993 | 6/1990 | McClelland | 2/424 |
| 5,073,324 | 12/1991 | Beaudet | 2/426 |
| 5,182,817 | 2/1993 | Branum | 2/439 |
| 5,184,354 | 2/1993 | Alfaro et al. | 2/425 |
| 5,206,955 | 5/1993 | Milligan | 2/9 |
| 5,216,759 | 6/1993 | Hewitt et al. | 2/431 |
| 5,267,353 | 12/1993 | Milligan | 2/9 |
| 5,438,710 | 8/1995 | McDonald et al. | 2/426 |

FOREIGN PATENT DOCUMENTS

| | | | |
|---|---|---|---|
| 2056790 | 6/1993 | Canada . | |
| 374131 | 4/1923 | Germany . | |
| 3400494 | 7/1984 | Germany | 2/426 |
| 469190 | 2/1952 | Italy . | |
| 5-64673 | 3/1993 | Japan . | |
| 148387 | 1/1955 | Sweden . | |
| 94/16654 | 8/1994 | WIPO | 2/426 |

*Primary Examiner*—Michael A. Neas
*Attorney, Agent, or Firm*—Richard A. Jordan

[57] ABSTRACT

New face masks protect a wearer's eyes against impact by a projectile or the like. In one aspect, the face mask comprising a plurality of frames, each of which is adapted to fit onto the wearer's face around one of the wearer's respective eyes, with each frame having mounted thereon a bar arrangement comprising a plurality of generally vertically directed protective bars. The bars are variably spaced in a horizontal direction and mounted into the respective frames so as to avoid obscuring the wearer's vision in any direction of the wearer's field of vision when both frames mounted onto the wearer's face. A "frame mounting arrangement," which in one embodiment includes a nose guard that is mounted between the frames to be situated over the wearer's nose, and a strap attached to both frames to extend behind the wearer's head, holds both the frames onto the wearer's face such that one of the frames is fitted around one of the wearer's eyes. In various embodiments, the nose guard enables the positions of the frames to be adjusted relative to the nose guard so that they may conform to varying facial contours. In another aspect, in addition to or instead of a bar arrangement a lens arrangement is provided, in which a lens is mounted in one or both frames. To accommodate a lens each frame defines a rim receiving area including an peripheral surface, a ridge extending inwardly from the peripheral surface, and a rear surface depending perpendicularly from the peripheral surface. Each lens' rim, in turn, has an exterior surface having a groove formed therein and a perpendicular rear surface, each rim being adapted so that, when it is mounted onto a respective the frame, the rim's perpendicular rear surface abuts the rear surface of the rim receiving area and the ridge extends into the groove. The rim receiving area's rear surface cooperating with the rim's perpendicular rear surface to inhibit rearward movement by the rim, and the ridge cooperating with the groove to inhibit forward movement by the rim, thereby to facilitate holding of the rim in the respective frame.

5 Claims, 5 Drawing Sheets

DEVICE FOR PROTECTING FACE AND EYES AGAINST PROJECTILE IMPACT

FIELD OF THE INVENTION

The invention relates generally to the field of protective devices and more particularly to devices such as face masks, spectacles (that is, eyeglasses) and the like for protecting the eye and face against impact from projectiles.

BACKGROUND OF THE INVENTION

In many activities, it is important to protect the eye against impact from a number of, for example, high-velocity projectiles which may be found in a person's environment. For example, many sporting activities, such as handball, racketball, squash and the like, are played in a confined area, and the handballs, racketballs, etc., may bounce off a myriad of surfaces, including walls, floor and ceiling, which define the area, and approach a participant from any of a number of directions.

Many arrangements have been developed to provide protection to the eye against such impact. In some protective arrangements, the eye protection is integral with elements, such as helmets, which serve to protect other parts of the head against impact. In such arrangements, typically bars may be unidirectionally arrayed or arrayed in a grid fashion over the wearer's eyes to protect them against impact. One problem with such devices is that the bars typically tend to obscure the wearer's vision at least in some viewing directions of the wearer's field of view, which can be detrimental particularly in activities in which the projectiles can move quite rapidly.

In addition, typically helmet-type devices are often uncomfortable, expensive and generally unnecessary in a number of sporting activities. In those activities, other protective arrangements, such as goggles or safety glasses, may find greater utility. Generally, goggles or safety glasses make use of lenses made of plastic or other clear material, with the lenses being mounted in frames which direct the impact force to areas of the wearer's face such as the cheeks and forehead. The lenses may the used to assure that the wearer's field of view will not be obscured by protective bars which are used in the helmet arrangements described above, and they may also be used to provide vision correction for the wearer. However, generally the lenses may not be able to withstand impact forces as high as those which can be withstood by the protective bars, since they may shatter or be forced out of their frames at lower impact forces. This is particularly true of corrective lenses, since the manufacturing process for spectacles including corrective lenses typically requires that the lenses be inserted into a frame rather than being integrally molded with the frame. In addition, goggles and safety glasses often direct the impact force to generally limited areas of the wearer's face, which can lead to discomfort or injury in those areas.

SUMMARY OF THE INVENTION

The invention provides new and improved devices, such as face masks, spectacles (that is, eyeglasses) and the like for protecting the eye and face against impact.

In brief summary, in one aspect the invention provides a new face mask for protecting a wearer's eyes against impact by a projectile or the like. The face mask comprises a plurality of frames, each of which is adapted to fit onto the wearer's face around one of the wearer's respective eyes, with each frame having mounted thereon a bar arrangement comprising a plurality of generally vertically directed protective bars. The bars are variably spaced in a horizontal direction and mounted into the respective frames so as to avoid "simultaneous scatoma," that is, to avoid obscuring the wearer's vision from both eyes at the same time in any direction of the wearer's field of vision when both frames mounted onto the wearer's face. A "frame mounting arrangement," which in one embodiment includes a nose guard that is flexibly mounted between the frames to be situated over the wearer's nose, and a strap attached to both frames to extend behind the wearer's head, holds both the frames onto the wearer's face such that the frames be fitted fairly snugly around respective ones of the wearer's eyes to hold the bars in front thereof to protect the eyes from projectiles. In various embodiments, the nose guard enables the positions of the frames to be adjusted relative to the nose guard so that they may conform to varying facial contours.

In another aspect, the invention provides a face mask for protecting a wearer's eyes against impact by a projectile or the like. The face mask comprising a plurality of frames, each of which is adapted to fit onto the wearer's face around one of the wearer's respective eyes, with each frame having mounted thereon a lens arrangement. The lens arrangement includes a plurality of lenses, each adapted to be mounted on the frame. In one embodiment, to accommodate a respective lens each frame defines a rim having a rear peripheral surface depending generally perpendicularly therefrom. Each lens' rim, in turn, has an exterior surface and a perpendicular rear surface, each rim being adapted so that, when it is mounted onto a respective frame, the rim's perpendicular rear surface abuts the rear surface of the rim receiving area. The lens's rear surface cooperates with the rim's perpendicular rear surface to inhibit rearward movement by the lens if the lens is impacted.

In one embodiment, the rim further has a lens retaining arrangement which cooperates with the lens to inhibit forward movement by the lens after the lens has been mounted in the frame. A "frame mounting arrangement," which in one embodiment includes a nose guard that is flexibly mounted between the frames to be situated over the wearer's nose, and a strap attached to both frames to extend behind the wearer's head, holds both the frames onto the wearer's face such that one of the frames is fitted around one of the wearer's eyes.

BRIEF DESCRIPTION OF THE DRAWINGS

This invention is pointed out with particularity in the appended claims. The above and further advantages of this invention may be better understood by referring to the following description taken in conjunction with the accompanying drawings, in which:

DETAILED DESCRIPTION OF AN ILLUSTRATIVE EMBODIMENT

Figure 1:
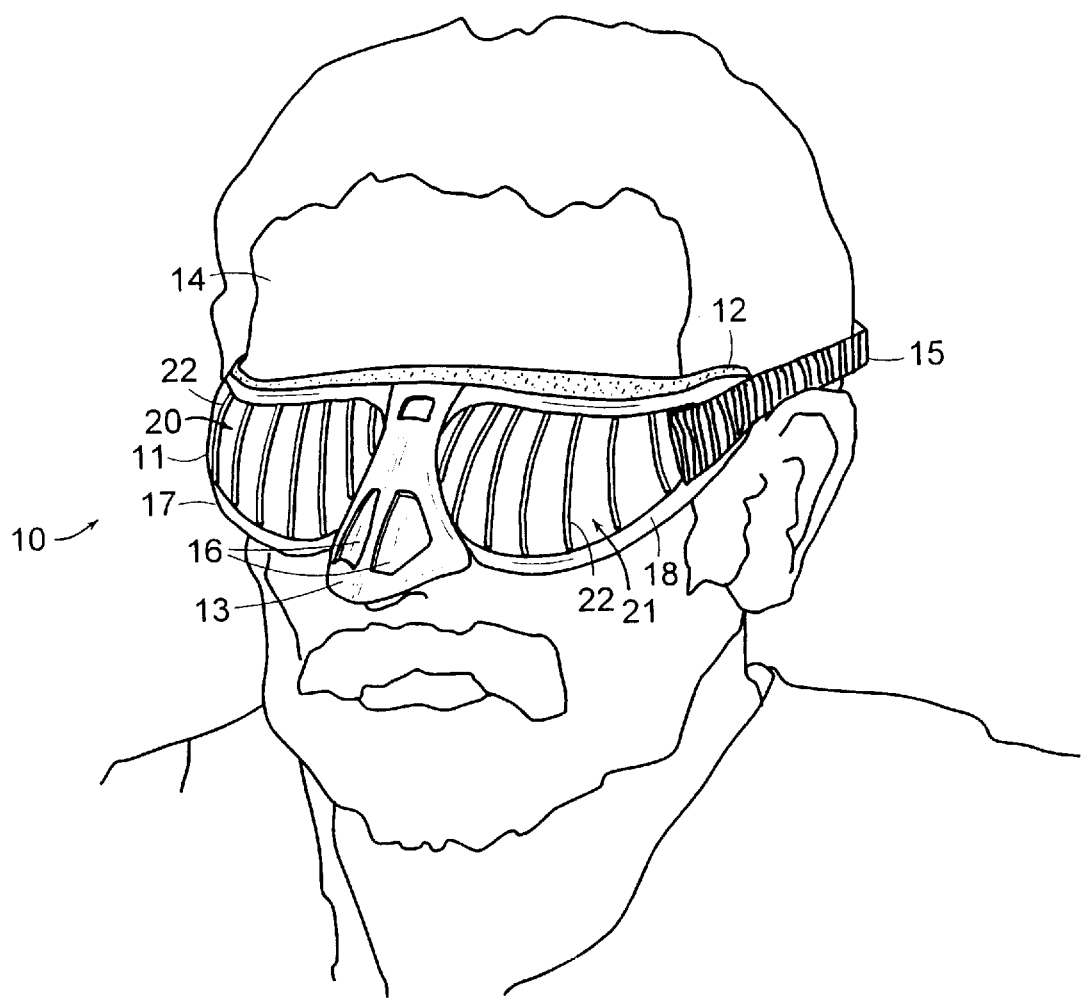
FIG. 1 is a diagram illustrating a new protective face mask constructed in accordance with one aspect of the invention.

FIG. 1 is a diagram illustrating a new protective face mask 10 constructed in accordance with the invention. With reference to FIG. 1, the face mask 10 includes two eye guard portions 11 and 12, pivotally mounted on opposing sides of a nose guard portion 13. As shown in FIG. 1, a person (generally identified by reference numeral 14) wears the face mask 10, with the nose guard portion 13 overlying the person's nose and the eye guard portions 11 and 12 being worn over the person's eyes on opposing sides of his or her nose. An adjustable band 15 connected to each of the eye guard portions 11 and 12 extends around the back of the person's head to hold the face mask in place on the face. The face mask 10 is generally intended to be used in a number of applications, for example, in sporting, industrial and military applications, to resist impact of projectiles directed primarily toward the eyes and nose. In particular, projectiles that would otherwise impact the eye or nose region, in particular, any portion of the face which is covered by the face mask 10, impact the face mask 10 instead, and the face mask is designed to cushion and efficiently distribute the impact forces over the wearer's face. In addition, the face mask 10 is designed to minimize the likelihood that the wearer's vision will be obscured, so that the wearer can, if he or she so desires, maintain the projectile in his or her field of vision.

The pivotal mounting of the eye guard portions 11 and 12 on the nose guard portion 13 allows the positions of the eye guard portions 11 and 12 to be adjusted relative to the nose guard portion 13 to accommodate to the shape of the face when the face mask 10 is worn. The nose guard portion 13 is formed to have a suitable contour to conform to a person's nose, and is fabricated from a suitable material, such as a high-impact resistant plastic material. In one embodiment, depicted in FIG. 1, the nose guard portion 13 has a number of apertures 16 formed therein which permit evaporation of perspiration which may develop under the nose guard portion 13 while the face mask 10 is being worn.

As noted above, the rotational position of each of the eye guard portions 11 and 12 is adjustable with respect to the nose guard portion 13 to allow the face mask 10 to accommodate the shape of the face of the wearer. Each of the eye guard portions 11 and 12 is formed from a generally eccentrically-shaped frame 17 and 18 on which is mounted an eye protection element 20 and 21. In accordance with one aspect of the invention, as depicted in FIG. 1, the eye protection elements 20 and 21 comprise generally vertically-extending bars, generally identified by reference numeral 22, which serve to resist passage of projectiles, such as balls, which may be directed at and otherwise impact the eye. Each of the frames 17 and 18 has a contour proximate the nose guard portion 13 which generally conforms to the adjacent contour of the nose guard 13. In addition, each of the frames 17 and 18 has a contour distant from the nose guard 13 which tapers to provide a ridge to which the band 15 is attached. The frames 17 and 18 of the respective eye guard portions 11 and 12 serve to distribute forces which are developed when a projectile impacts the eye guard portions 11 and 12 over the portions of the face proximate thereto, which will reduce forces which may develop at any particular point. In addition, the rear surfaces of the frames 17 and 18 are preferably provided with a cushion, which will also serve to absorb impact energy, which can both diminish the instantaneous impact forces which are developed and may serve to distribute the forces over time following impact. The cushion may be similar to the cushion 41 described below in connection with the embodiment described in FIGS. 5 and 6; in that embodiment, the cushion comprises a fairly rigid forward cushion formed from material such as urethane, with a more resilient rear cushion formed from a material such as Ensolite, which sits on the wearer's face. The rear cushion preferably has a hysteresis so that it will compress generally rapidly when the face mask is impacted, but will return to the pre-impact condition fairly slowly to avoid rapid and uncomfortable movements by the face mask 10.

As noted above, the eye guard portions' eye protection elements 20 and 21 include a number of bars 22 which serve to resist passage of projectiles which may be directed at and otherwise impact the eye positioned therebehind. The bars 22 are generally vertically directed across the field of vision of the person wearing the face mask 10, and are generally bowed outwardly to define a generally convex configuration. The convex configuration ensures that impact forces will be generally directed to the respective frame 17 or 18, and reduces the likelihood that an impact will force the bar(s) 22 rearwardly toward the eye. The bars 22 may be affixed to the frames 17 and 18 in any convenient manner, such as by molding the ends of the bars 22 into the respective frames 17 and 18. (In addition, the bars 22 may be mounted in the frames 17 and 18 in a manner similar to the embodiment described below in connection with FIGS. 5 and 6, as will be described in connection with those FIGs.) The bars 22 are preferably formed of a relatively stiff but resilient material, such as a metal, which can provide a spring action to deflect at most slightly when struck by a projectile, but which will not generally be so rigid as to break or shatter when struck. Alternatively they may be molded of a tough plastic resin with or without a reinforcing filler such as a glass or carbon fiber.

In accordance with one aspect of the invention, the bars 22 are variably spaced apart and arranged across the field of vision in such a manner as to avoid "simultaneous scatoma," that is, to avoid obscuring the wearer's vision from both eyes at the same time in any direction of the wearer's field of vision when both frames mounted onto the wearer's face; that is regardless of the viewing direction, vision by at least one of the eyes will not be obscured by the bars 22. Otherwise stated, if a bar 22 is positioned so as to obscure vision by one of the eyes, such as the right eye, when that (right) eye is viewing in a particular direction, no bar 22 will be positioned so as to obscure vision by the left eye when that (left) eye is viewing in the same direction. Similarly, if a bar is positioned so as to obscure vision by the left eye when that (left) eye is viewing in a particular direction, no bar will be positioned so as to obscure vision by the right eye when that (right) eye is viewing in the same direction. Thus, the eye protection elements 20 and 21 are configured to ensure that vision by at least one of the eyes will not be obscured, so that the wearer can always maintain the projectile in his or her field of vision.

Figure 2:
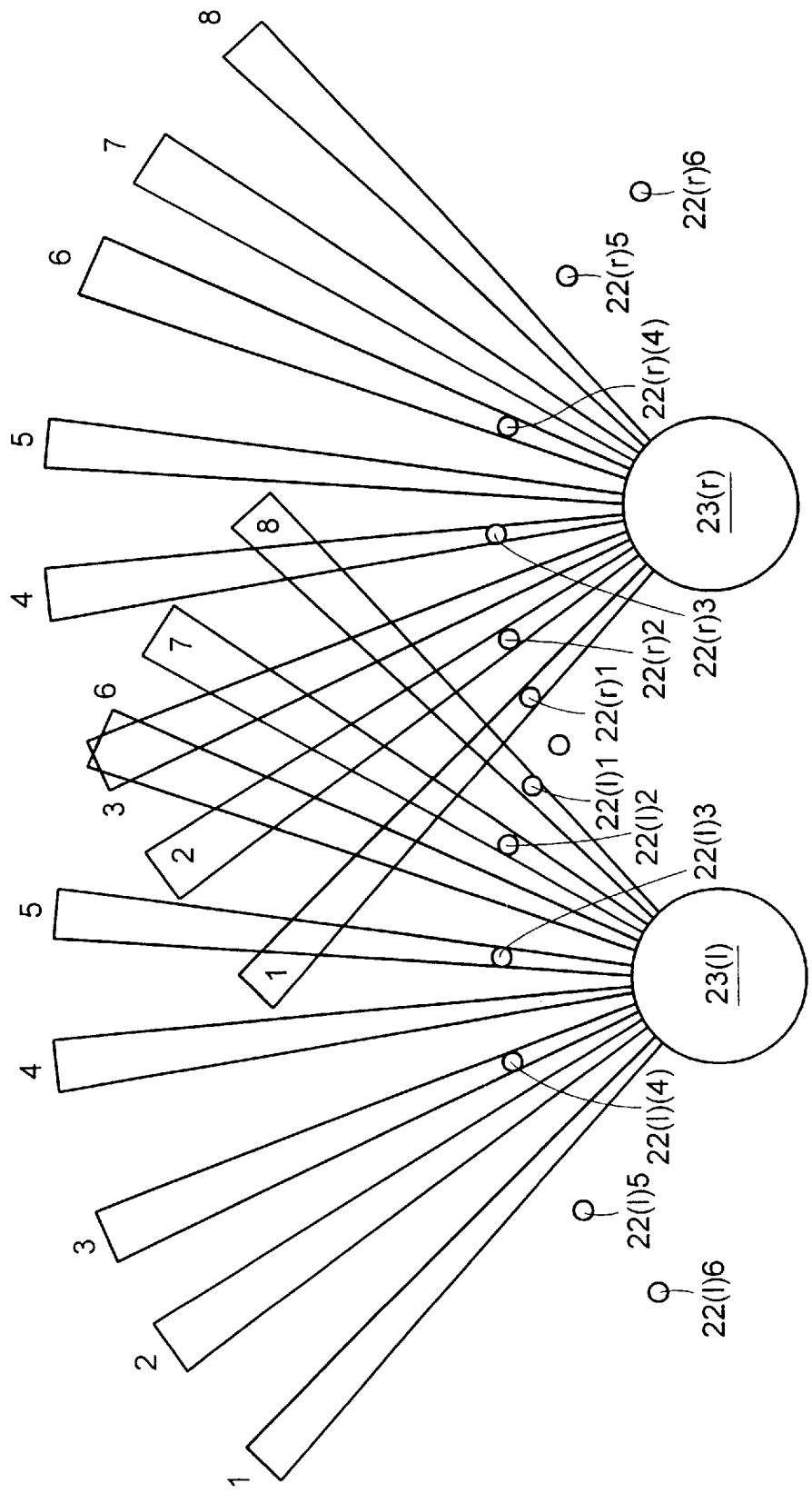
FIG. 2 is a schematic diagram useful in understanding the structure of the protective face mask depicted in FIG. 1.

This will be described in connection with FIG. 2. FIG. 2 is a ray diagram that schematically depicts the configuration of the 22 in front of the wearer's eyes, which are located at points 23(l) and 23(r), with point 23(l) representing the location of the left eye and point 23(r) representing the location of the right eye. In the embodiment depicted in FIG. 2, six bars are associated with each eye, with the bars associated with the left eye being identified by reference numerals 22(l)(1) through 22(l)(6) (generally identified by reference numeral 22(l)(n)) and the bars associated with the right eye being identified by reference numerals 22(r)(1) through 22(r)(6) (generally identified by reference numeral 22(r)(n)). Bars 22(l)(n) and 22(r)(n) for lower values of "n" are proximate the location of the nose guard portion 13 (not shown), with bars 22(l)(n) and 22(r)(n) for increasing values of "n" being positioned progressively away from the nose guard portion 13. In the embodiment shown in FIG. 2, the spacings between adjacent bars 22(l)(n) and 22(l)(n+1), on the one hand, and 22(r)(n) and 22(r)(n+1), on the other hand, increases for increasing "n," that is, from the center proximate the nose guard portion 13 in an outward direction. Accordingly, the spacing between bars 22(l)(1) and 22(l)(2) is less than the spacing between bars 22(l)(2) and 22(l)(3), and so forth for successive each pair of bars for increasing values of "n." Similarly, the spacing between bars 22(r)(1) and 22(r)(2) is less than the spacing between bars 22(r)(2) and 22(r)(3), and so forth for each successive pair of bars for increasing values of "n."

The variation in the spacings between proximate bars 22(l)(n) and 22(r)(n) assists in providing that the wearer's field of vision will not be obscured by the bars, regardless of the direction in which the wearer is viewing. This will be described in connection with a number of rays depicted in FIG. 2. Also shown in FIG. 2 are eight ray envelopes, numbered 1 through 8, extending from each of points 23(l) and 23(r), with each pair of similarly-numbered rays representing one of a number of viewing directions in the field of vision defined by points 23(l) and 23(r). The similarly-numbered ray envelopes extending from each point 23(l) and 23(r) represent the same viewing direction, so that, for example, the direction represented by ray envelope 1 extending from point 23(l) represents the same viewing direction as the direction represented by ray envelope 1 extending from point 23(r). Similarly, the direction represented by ray envelope 2 extending from point 23(l) represents the same viewing direction as the direction represented by ray envelope 2 extending from point 23(r), and generally, the direction represented by ray envelope "m" ("m" being an integer from "1" to "9") extending from point 23(l) represents the same viewing direction as the direction represented by ray envelope "m" extending from point 23(r).

As noted above, the spacings and locations of the bars 22(l)(m) and 22(r)(m) provide that viewing by at most one eye will be obscured regardless of the direction in which the wearer is looking in the field of view. Thus, as shown in FIG. 2, while from point 23(r) the viewing direction represented by ray envelope "1" extending from point 23(r) will be obscured by bar 22(r)(1), the bars 22(l)(4) and 22(l)(5) are positioned so as to avoid obscuring the viewing direction represented by ray envelope "1" extending from point 23(l). On the other hand, while from point 23(l) the viewing direction represented by ray envelope "8" will be somewhat obscured by bar 22(l)(1), the bars 22(r)(4) and 22(r)(5) are positioned so as to avoid obscuring the viewing direction represented by ray envelope "8" extending from point 23(r).

Similarly, while from point 23(l) the viewing directions represented by ray envelopes "3," "5" and "7" extending from point 23(l) will be obscured by bars 22(l)(4), 22(l)(3) and 22(l)(1), respectively, the bars 22(r)(n) (in particular, bars 22(r)(2) and 22(r)(3) in the case of ray envelope 3 extending from point 23(r), bars 22(r)(3) and 22(r)(4) in the case of ray envelope 5 extending from point 23(r), and bars 22(r)(4) and 22(r)(5) in the case of ray envelope 7 extending from point 23(r)) are positioned so as to avoid obscuring the viewing direction represented by ray envelopes 3, 5 and 7 extending from point 23(r). On the other hand, while from point 23(r) the viewing directions represented by ray envelopes "2," "4" and "6" extending from point 23(r) will be obscured by bars 22(r)(2), 22(r)(3) and 22(r)(4), respectively, the bars 22(l)(n) (in particular, bars 22(l)(5) and 22(l)(4) in the case of ray envelope 2 extending from point 23(l), bars 22(l)(4) and 22(l)(3) in the case of ray envelope 4 extending from point 23(l), and bars 22(l)(3) and 22(l)(2) in the case of ray envelope 6 extending from point 23(l)) are positioned so as to avoid obscuring the viewing direction represented by ray envelopes 2, 4 and 6, respectively extending from point 23(l).

Thus, the spacings and locations of protective bars 22 on the respective eye guard portions 11 and 12 of the face mask described above in connection with FIGS. 1 and 2 are selected in such a manner as to ensure that at most one of the wearer's eyes will be obscured by a bar 22, regardless of the direction in which the wearer is viewing, thereby to ensure that all portions of the wearer's full field of view is available to him or her at all times. Accordingly, the wearer will be able to see all aspects of his or her environment, such as projectiles, physical obstructions such as walls or the like, and so forth at all times.

It will be appreciated that numerous variations may be made in the embodiment described above in connection with FIGS. 1 and 2. For example, instead of providing a uniformly increasing separation of bars 22 outwardly from the nose guard portion 13, the bar separation may instead uniformly decrease, and indeed it may be non-uniform. In addition, a single frame may be provided which would support the bars in front of both the wearer's eyes; in that case no nose guard portion need be provided.

Figure 4:
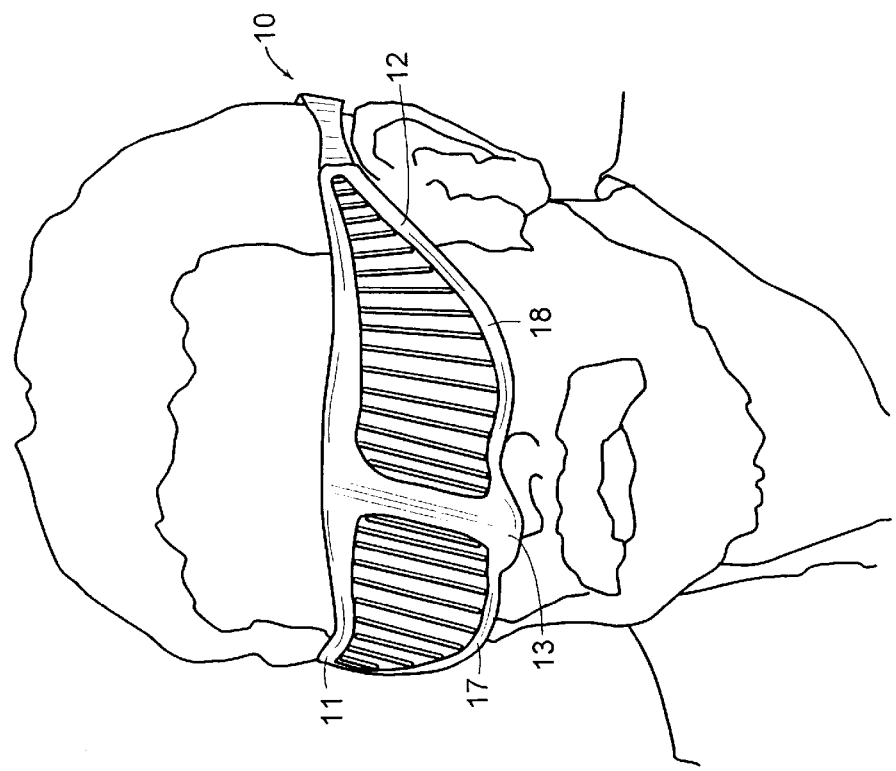
FIGS. 3 and 4 are diagrams illustrating variations in the face mask described above in connection with FIGS. 1 and 2.
Figure 3:
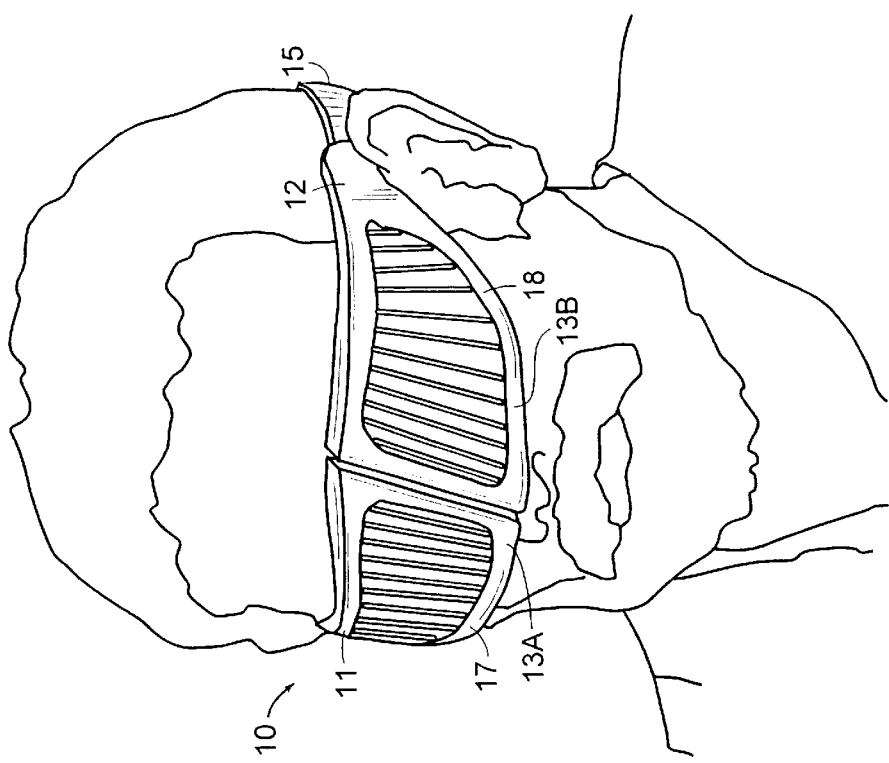

In addition, if the face mask includes a nose guard portion, numerous modifications may be made to the nose guar portion. FIGS. 3 and 4 illustrate respective variations primarily in connection with the nose guard portion 13 and the mounting of the eye guard portions 11 and 12 thereto. In the embodiment depicted in FIG. 3, the nose guard portion is divided into two elements, identified by reference numeral 13A and 13B, which are hinged together proximate the center of the wearer's nose so that the face mask 10 can adjust to conform to the wearer's face. In that embodiment, each element 13A and 13B will be formed integral with the proximate eye guard portion 11 and 12, so that essentially the respective portions of the eye guard portions' frames 17 and 18 proximate the wearer's nose, overlies the nose and cooperate to form the nose guard portion 13.

On the other hand, FIG. 4 depicts an embodiment in which the nose guard portion 13 is formed unitary with the eye guard portions 11 and 12. In the embodiment depicted in FIG. 4, the nose guard portion and the eye guard portions' frames 17 and 18 may be formed from a generally flexible material, so that the face mask will adjust to conform generally to the wearer's face.

In the embodiments depicted in FIGS. 3 and 4, the respective nose guard portions 13 are not shown as being provided with apertures 16 (FIG. 1) to facilitate evaporation of perspiration. However, it will be appreciated that such apertures may be provided in those embodiments.

In addition, the mask 10 may be provided without a nose guard portion 13. In that case, a bridge (not shown) may be provided which is sized to fit over the bridge of the wearer's nose, and the frames 17 and 18 may be hinged to the bridge, or the bridge may be formed unitary with the frames 17 and 18 and hinged proximate the center of the wearer's nose.

Figure 5:
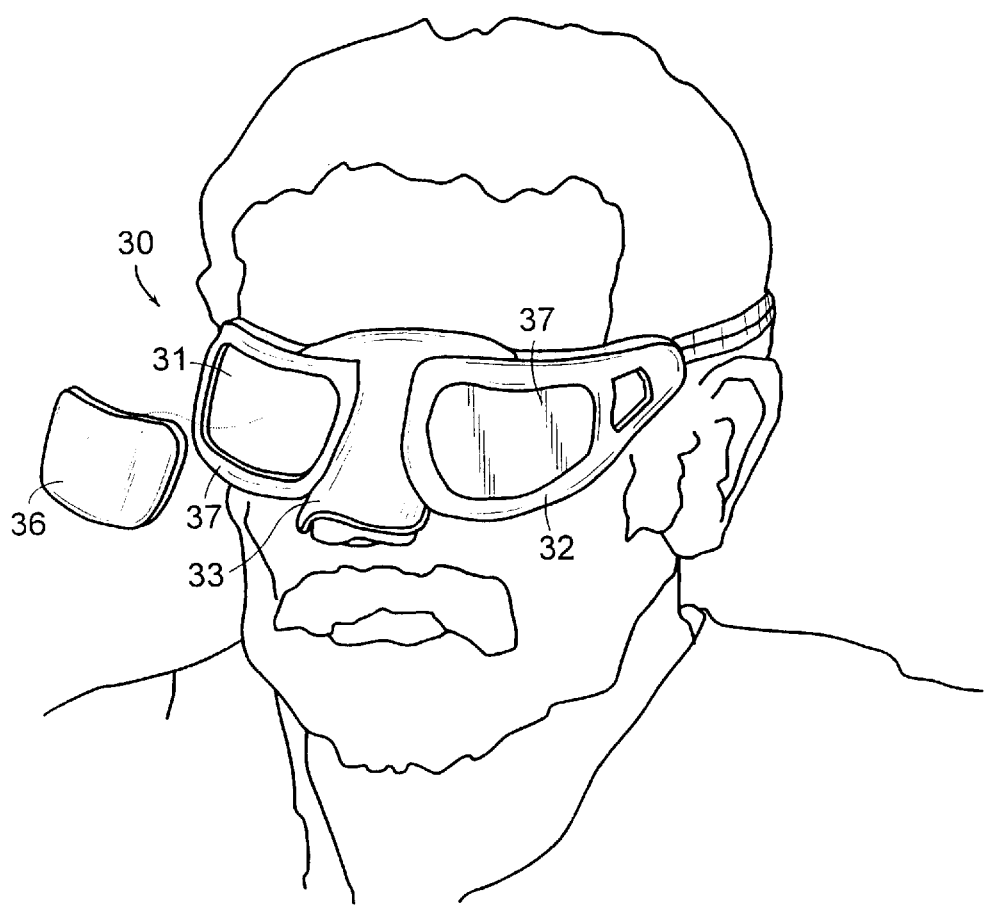
FIGS. 5 is a diagram illustrating a new protective face mask constructed in accordance with a second aspect of the invention.

A second aspect of the invention will be described in connection with FIGS. 5 and 6. With reference initially to FIG. 5, that FIG. depicts a face mask 30 having eye guard portions 31 and 32 both of which are pivotally mounted to opposing sides of a nose guard portion 33. The nose guard portion 33 may be similar to the nose guard portions 13 or 13A and 13B described above in connection with FIGS. 1, 3 and 4. As with face mask 10, each of the eye guard portions 31 and 32 includes a cushioned frame 34 and 35. Each of the eye guard portions 31 and 32 includes respective lenses 36 and 37 which may be utilized to provide protection against impact. In addition, if the wearer requires use of corrective lenses to correct for deficiencies in his or her vision, the lenses 36 and/or 37 may be formed to provide the required correction. The lenses 36 and/or 37 may be used instead of or in addition to the bars 22 described above in connection with FIGS. 1 through 4. If the bars 22 are provided in addition to the lenses 36 and 37, preferably they (that is, the bars 22) will be provided exteriorly of the lenses 36 and 37 so that projectiles will likely impact the bars 22 instead of the lenses.

In accordance with the invention depicted in FIGS. 5 and 6, a new and improved arrangement for mounting of the lenses 36 and 37 is provided, which will be described in connection with FIG. 6. Generally, the lens mounting arrangement depicted in FIG. 6 minimizes the likelihood that the lens, if impacted by a projectile, will be forced rearwardly into the eye of the wearer of the face mask 30. FIG. 6 depicts a partial cross sectional view of a portion of the face mask 30 depicted in FIG. 5, in particular a partial cross section of the eye guard portion 31, showing a cross section of a portion of the cushioned frame 34 and a portion of the lens 36 proximate the frame 34. The frame 34 comprises a lens holder 40 which is mounted in a rear cushion 41. The cushion 41, in turn, has a rear surface 42 that abuts the wearer's face. As shown in FIG. 6, the lens holder 40 defines surfaces 43 and 44 that extend inwardly in a recess 45 in the cushion. The surfaces 43 and 44, in turn, define outwardly extending ridges 46 and 47 that mate with corresponding locking recesses 50 and 51 in the cushion, which hold the lens holder 40 in place. As with the face mask 10, the cushion 41 preferably includes a fairly rigid forward cushion 70 formed from material such as urethane, with a more resilient rear cushion 71 formed from a material such as Ensolite, which sits on the wearer's face. The rear cushion preferably has a hysteresis so that it will compress generally rapidly when the face mask is impacted, but will return to the pre-impact condition fairly slowly to avoid rapid and uncomfortable movements by the face mask 30. Preferably, the rear cushion 71 will be provided with gaps which will facilitate ventilation in the space to the rear of the face mask 30 and in front of the wearer's eyes.

The lens holder 40, in turn, holds the lens 36 in place in the eye guard portion 31. As shown in FIG. 6, the lens holder 40 is provided with a lens receiving area 52 comprising peripheral surface 54 having depending therefrom a generally perpendicular rear surface 53 and a ridge 55. The lens 36 has a rear surface 57 that abuts the rear surface 53 of the lens receiving area, and a notch 55 formed in its rim 58 that serves to receive the ridge 55 when it (the lens 36) is inserted into the lens holder 40. The lens 36 is inserted into the lens holder 40 from the front and is pushed rearwardly toward the rear surface 53 of the lens holder's lens receiving area 52. The lens preferably has a beveled rear corner 60 and the ridge 55 preferably has an inclined forward surface 56 and, when the lens 36 is pushed rearwardly, the bevel of the rear corner 60 forces the ridge 55 slightly outwardly, causing the lens holder 40 to deflect outwardly (that is, away from the lens 36) slightly. When the lens 36 is fully inserted in the lens holder 40, the rear surface 57 rests against the rear surface 53 of the lens holder's lens receiving area 52.

The perpendicular rear surface 53 of the lens receiving area 52 generally prevents the lens from being forced out of the lens holder 40 in a rearward direction by impact of a projectile on the forward surface of the lens 36. It will be appreciated that, if projectiles directed against the lens 36 have sufficiently high rearward impact forces, the lens 36 may, indeed, be forced rearwardly out of the lens holder and towards the wearer's eye, but the perpendicular rear surface 53 may be dimensioned to either require a force that is unlikely to be provided before that will occur.

Figure 6:
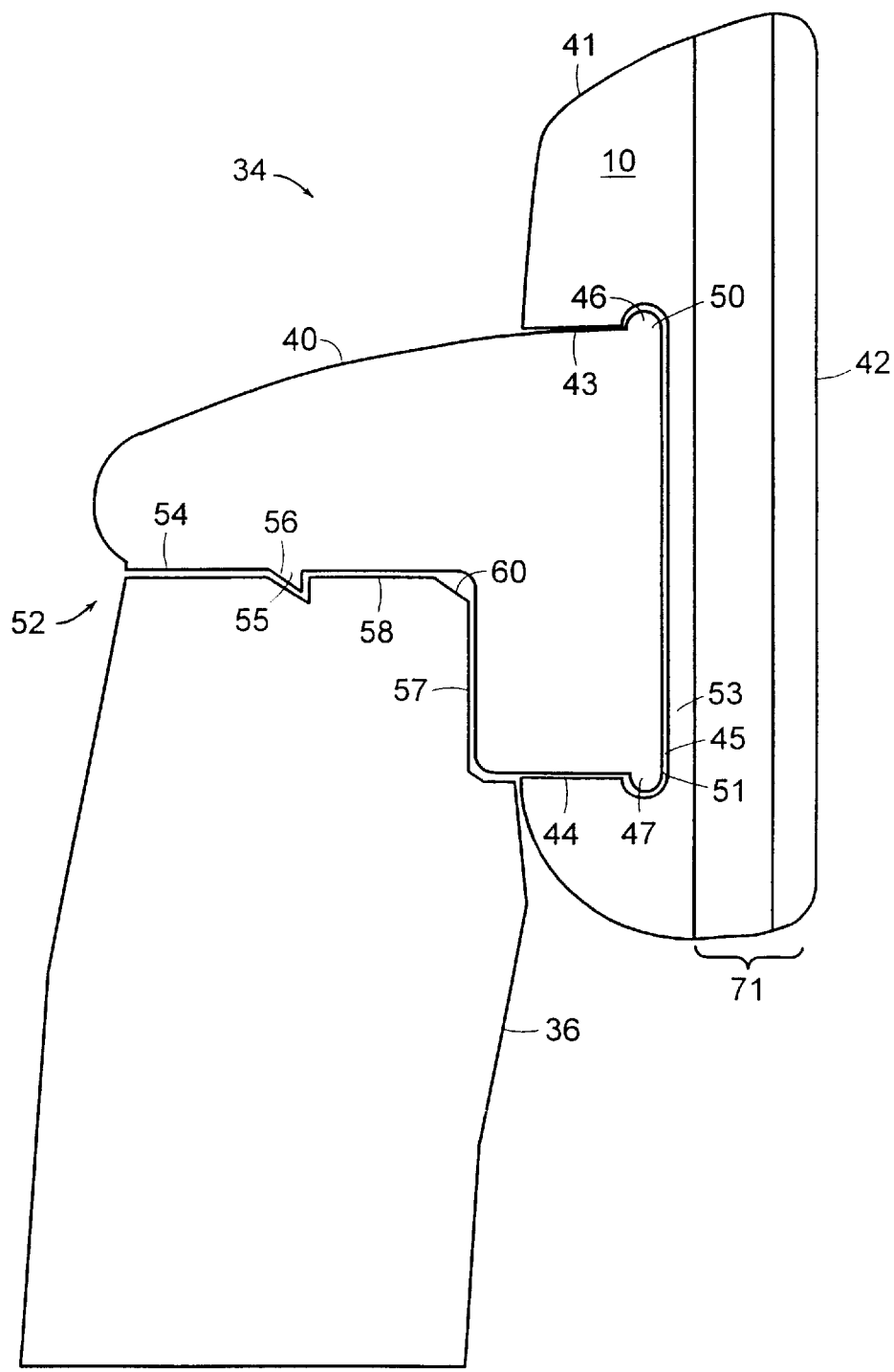
FIG. 6 is a diagram, in section, depicting a detail of a portion of the face mask depicted in FIG. 5.

The ridge 55 and notch 56, on the other hand, provide an impedance that inhibits the lens 36 from being forced out of the lens holder 40 in a forward direction, that is, in a direction to the left as shown in FIG. 6 (the direction away from the wearer's face when the face mask is being worn). However, the ridge 55 and notch 56 substantially smaller than the perpendicular rear surface 53 of the lens receiving area 52, in which case a substantially smaller force would be required to force the lens 36 out of the lens holder 40 in a forward direction. Since this direction is generally away from the wearer's face when the face mask is being worn, it would be unlikely that injury would occur if the lens 36 were to be forced out of the lens holder 40 in this direction.

As noted above in connection with FIG. 1, the bars 22 used in the face mask 10 may be mounted in the frames 17 and 18 in a manner similar to the embodiment described below in connection with FIGS. 5 and 6, as will be described in connection with those FIGs. In such a mounting arrangement, the bars may be affixed to a rim (not shown) which has a periphery which has a notch formed therein which is similar to the notch 55 in lens 36. Preferably, the rim will also have a perpendicular rear surface which is similar to the perpendicular surface 57 of lens 36. In addition, the frames 17 and 18 will be constructed generally similar to frame 34 described above in connection with FIG. 6, in particular including a rear surface 57 and ridge 56. The mounting arrangement's rim may be inserted into respective frames 17 and 18 in a manner similar to the manner in which the lenses 36 and 37 are mounted in the frames provided for the face mask 30, so that the perpendicular rear surface of the rim (that is, the rim of the mounting arrangement used for face mask 10) will abut the perpendicular surface of the frame, and the notch of the rim (that is, the notch of the mounting arrangement used for face mask 10) will receive the ridge. Such a mounting arrangement for face mask 10 may have several advantages. For example, the mounting arrangement may allow the same frames to be used for both face mask 10 (which uses bars 22 to provide eye protection) and face mask 30 (which uses lenses 36 and 37 to provide eye protection and may also provide for vision correction), which may reduce manufacturing costs. In addition, a wearer may be able to interchangeably use the bar eye protection (reference face mask 10) for some activities and lens eye protection (reference face mask 30) for other activities, without having to purchase separate face masks 10 and 30.

It will be appreciated that numerous modifications may be made to the face mask 30. For example, although the lens holder's rear surface 54 has been described as being generally perpendicular to the peripheral surface 53 of the lens receiving area, the rear surface 54 may instead be disposed at another angle which is not necessarily perpendicular to the peripheral surface 53. In any case, the angle between the rear surface 54 and the peripheral surface 53 is selected to reduce or otherwise minimize the likelihood that forces generated in the lens due to an impact will be transferred to the lens hoder in a radially-outward direction, which may otherwise force the lens holder to enlarge slightly and allow the lens to be forced rearwardly toward the wearer's eye.

Furthermore, the face mask 30 has been described as including an arrangement including a ridge 55 in the lens holder 40 and groove 56 in the lens 36 for inhibiting forward movement of the lens out of the lens holder, it will be appreciated that the lens 36 may instead include a ridge 55 and lens holder 40 may instead include a mating groove. In that case, the lens need not be provided with a beveled rear corner 60. Alternatively, the lens holder 40 may be provided with a forward lip or ridge, which cooperates with the forward surface of the lens 36 to hold the lens in the frame; in that case the lens need not be provided with a mating groove.

Furthermore, although the face mask 30 has been described in connection with eye guard portions, each including a frame 34, 35 and associated lens 36, 37, respectively, the face mask 30 may instead be provided with a single eye guard portion including a frame and associated lens dimensioned to cover both of the wearer's eyes. In that case, the nose guard portion need not be provided.

The invention provides a number of advantages. In particular, it provides a face mask 10 or 30 which will provide a high degree of protection for, in particular the eyes, and also the nose, against impact from projectiles, which may be advantageously used in sporting, industrial, military and other applications. In one aspect, the face mask 10, using generally vertically-oriented bars 22 which are variably spaced across the wearer's field of vision, will provide protection while avoiding "simultaneous scatoma," that is, avoiding obscuring the wearer's vision from both eyes at the same time in any direction of the wearer's field of vision when both frames mounted onto the wearer's face. The bars 22 may be rigidly attached to the face mask 10, which will provide that they will not be forced out and into the wearer's eye. Alternatively, the bars 22 may be removably attached using a mounting arrangement which is similar to that used in connection with face mask 30, which provides a high degree of protection while also providing some advantages in manufacturing and flexibility by the user in interchanging the potential modes of protection. In a second aspect, the face mask 30, which provides lenses 36 and 37, also provides a high degree of protection, without requiring use of bars 22 to impede projectile impact. The lenses 36 and 37 may provide vision correction if required by the wearer. The lens mounts of face mask 30 are constructed to provide that the lenses will not be forced rearwardly toward the wearer's eyes when impacted by a projectile.

The foregoing description has been limited to a specific embodiment of this invention. It will be apparent, however, that various variations and modifications may be made to the invention, with the attainment of some or all of the advantages of the invention. It is the object of the appended claims to cover these and such other variations and modifications as come within the true spirit and scope of the invention.

What is claimed as new and desired to be secured by Letters Patent of the United States is:

1. A face mask for protecting a wearer's eyes against impact by a projectile or the like, the face mask comprising A. at least one frame adapted to fit onto the wearer's face around the wearer's eyes, B. at least one lens adapted to be removably mounted on a said frame, said lens including a rim, said frame further defining a rim receiving area including an peripheral surface and a rear surface that abuts said rim, the frame's rear surface depending from said peripheral surface at an angle which is selected to reduce or otherwise minimize the likelihood that forces generated in the lens due to an impact will be transferred to the frame in a radially-outward direction, which may force the frame to enlarge slightly and allow the lens to be forced rearwardly toward the wearer's eye, C. said frame further including a lens retainer for retaining the lens in said frame, the lens retainer including a ridge formed in the lens receiving area, and the lens including a groove formed in its peripheral surface, the ridge cooperating with the grove to inhibit forward movement by the rim, thereby to facilitate holding of the rim in the frame, the ridge being dimensioned to allow ready insertion of the lens into the frame and to inhibit forward movement by said lens relative to said frame.

2. A face mask as defined in claim 1 in which the frame's rear surface is disposed at an angle which is generally perpendicular to the frame's peripheral surface.

3. A face mask as defined in claim 1 further comprising a strap affixed to said frame adapted to extend around the rear of the wearer's head.

4. A face mask as defined in claim 3 in which the strap is adjustable.

5. A face mask as defined in claim 1 comprising two frames, each dimensioned to fit over one of the wearer's eyes, each frame having an associated lens.

* * * * *